United States Patent [19]
Higuchi et al.

[11] Patent Number: 5,916,925
[45] Date of Patent: Jun. 29, 1999

[54] PHARMACEUTICAL COMPOSITION FOR TREATMENT OF DEMENTIA

[75] Inventors: Shuji Higuchi, Frankfurt, Germany; Akinobu Nagaoka, Hyogo; Giichi Goto, Osaka, both of Japan; Reinhold Hübner, Kelkheim; Dietrich Hadler, Ruesselsheim, both of Germany

[73] Assignee: Takeda Chemical Industries, Ltd., Osaka, Japan

[21] Appl. No.: 08/791,804

[22] Filed: Jan. 30, 1997

[30]   Foreign Application Priority Data

Feb. 1, 1996 [JP] Japan ................................. 8-016912

[51] Int. Cl.⁶ ................................................. A61K 31/12
[52] U.S. Cl. .............................................. 514/678
[58] Field of Search ............................... 514/678

[56]   References Cited

U.S. PATENT DOCUMENTS 5,059,627  10/1991  Goto et al. ............................ 514/688

FOREIGN PATENT DOCUMENTS 0 629 400  12/1994  European Pat. Off. .

OTHER PUBLICATIONS

CAPLUS abstract Accession No. 1996:22520, Weyer et al. Hum. Psycholpharmacol. 11(1), 53–65, 1996.
Gutzmann et al., *Neurobiology of Aging,* vol. 17 (4 Suppl.) (1996) S141–S–142 XP000672169.
Miyamoto et al., *Society for Neuroscience Abstracts,* vol. 22 (1–3) 1996 p. 200 XP000672173.
ZS.–Nagy, *Arch. Gerontol. Geriatr.,* 1990, vol. 11, No. 3, pp. 177–186.
Bergamasco et al., *Funct. Neurol.,* May–Jun. 1994, vol. 9, No. 3, pp. 161–168.

*Primary Examiner*—Raymond Henley, III
*Attorney, Agent, or Firm*—Wenderoth, Lind & Ponack, L.L.P.

[57]   ABSTRACT

A pharmaceutical composition comprising idebenone of the present invention is useful for prevention of the progression of dementia.

16 Claims, 9 Drawing Sheets

\*\*   P< 0.01: comparison with A  (Dunnett test)
\#\#   P< 0.01: comparison with B  (Dunnett test)

—○—  :  Young rats group (n=10)
—●—  :  Control group (n=7)
—△—  :  Idebenone group (n=6)
—▲—  :  Compound A group (n=7)
—□—  :  Combination group (n=6)

PHARMACEUTICAL COMPOSITION FOR TREATMENT OF DEMENTIA

TECHNICAL FIELD

The present invention relates to a medicament for preventing or treating dementia comprising orally administering idebenone for more than 6 months and a pharmaceutical composition for prevention of the progression of dementia comprising idebenone, especially a method for orally administering idebenone for more than 6 months for the treatment of dementia; use of idebenone for the treatment of dementia comprising orally administering idebenone for more than 6 months; a pharmaceutical composition for prevention of the progression of dementia comprising idebenone, and so forth.

BACKGROUND ART

In parallel, an increase in the incidence of various adult diseases and central nervous system diseases, and an increasing aged population has posed a major social problem. How to treat patients with dementia, a central nervous system disease, in particular, is a quite an urgent problem to resolve. There have been no effective means of treating demented patients, especially those with senile dementia of Alzheimer's type or Alzheimer's disease, and prevention of the progression of dementia.

JP-A-3 81218 (U.S. Pat. No. 5,059,627) and JP-A-7 61923 (EP-A629400) disclose that idebenone is effective as a therapeutic agent for senile dementia of Alzheimer's type. JP-A-3 81218 discloses that the dosage of idebenone for adult humans is 0.1 mg to 500 mg per day. JP-A-7 61923 discloses a high dosage of idebenone of not less than 150 mg per day per adult.

In addition, Arch. Gerontol. Geriatr., Vol. 15, pp. 249–260 (1992) describes that idebenone proved to be effective in patients with senile dementia of Alzheimer's type when administered at 90 mg per day per adult.

However, the therapeutic methods described in these publications are characterized in that idebenone is administered for up to 6 consecutive months only and no more. There is no report regarding the potential of idebenone administration for safe prevention of dementia symptoms progression for an extended period of time.

In general, when administered at high doses, or for an extended period of time even at low doses, medicines often have adverse effects etc., which limit the desired patient treatment and hamper the obtainment of a satisfactory therapeutic effect. With regard to methods for preventing or treating dementia, especially senile dementia of Alzheimer's type and Alzheimer's disease, and prevention of the progression of dementia, no effective pharmaceuticals have been reported, except tacrine, a symptomatic drug. A long-term administration of tacrine is substantially impossible due to adverse effects such as hepatic toxicity. In fact, 74% of the patients receiving 30-week administration of tacrine withdrew from the treatment.

Against this background, the present inventors have found that excellent therapeutic effects or symptom progression-suppressing effects can unexpectedly be obtained very safely with minimum onset of adverse effects by administering idebenone for an extended period of time, especially for a period exceeding 6 months, as a method of preventing or treating and prevention of the progression of dementia, especially senile dementia of Alzheimer's type and Alzheimer's disease.

SUMMARY OF THE INVENTION

The present invention relates to a method of administering idebenone for not less than 6 months, as a method of preventing or treating patients with dementia or prevention of the progression of dementia, especially a method of treating patients with senile dementia of Alzheimer's type or Alzheimer's disease, or prevention of the progression of dementia.

DETAILED EXPLANATION OF THE INVENTION

Figure 1:
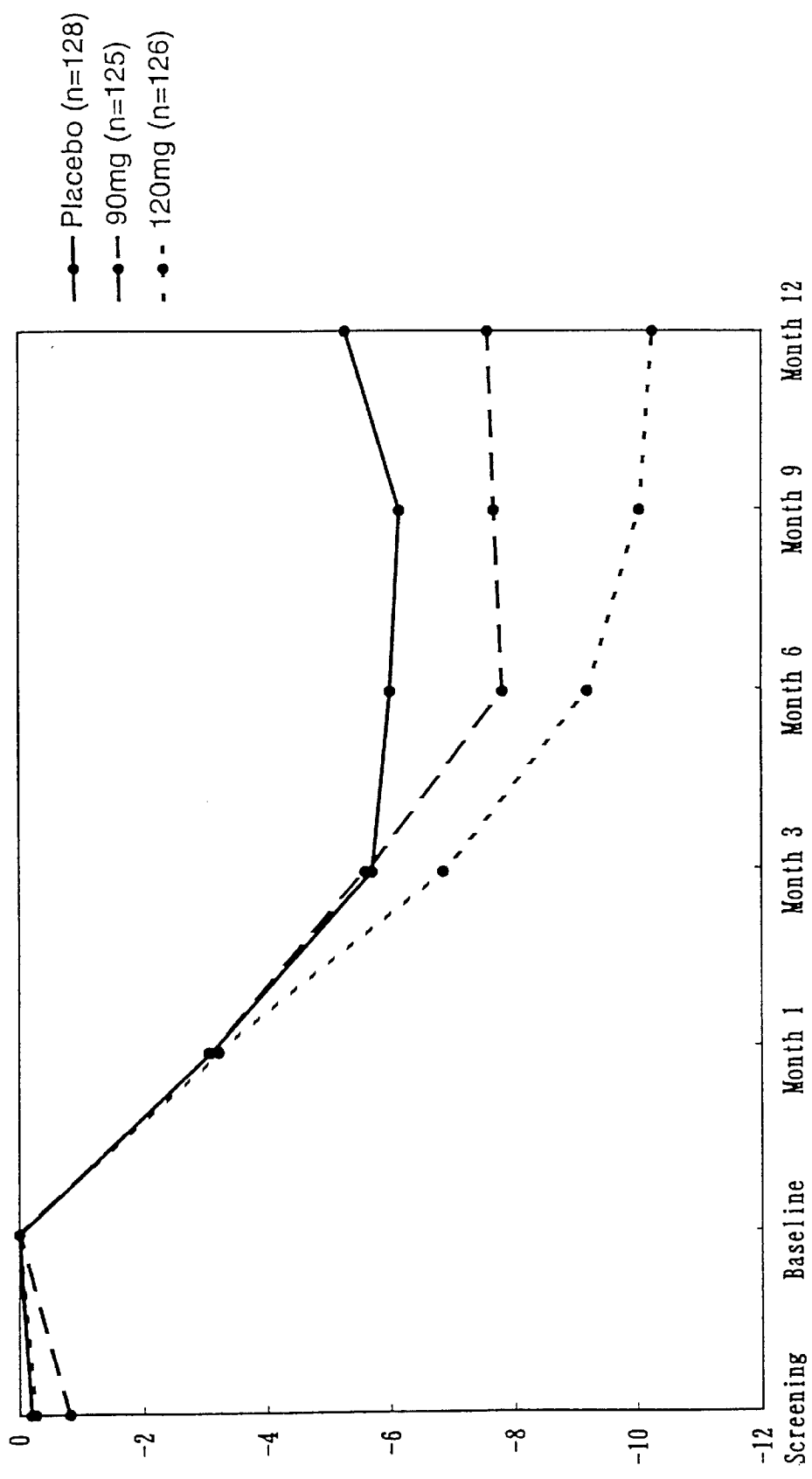
FIG. 1 shows the results of analysis of the clinical data obtained in Clinical Study Example 1, in terms of an efficacy parameter (ADAS Sum Score) shown in Clinical Study Example 1.
Figure 2:
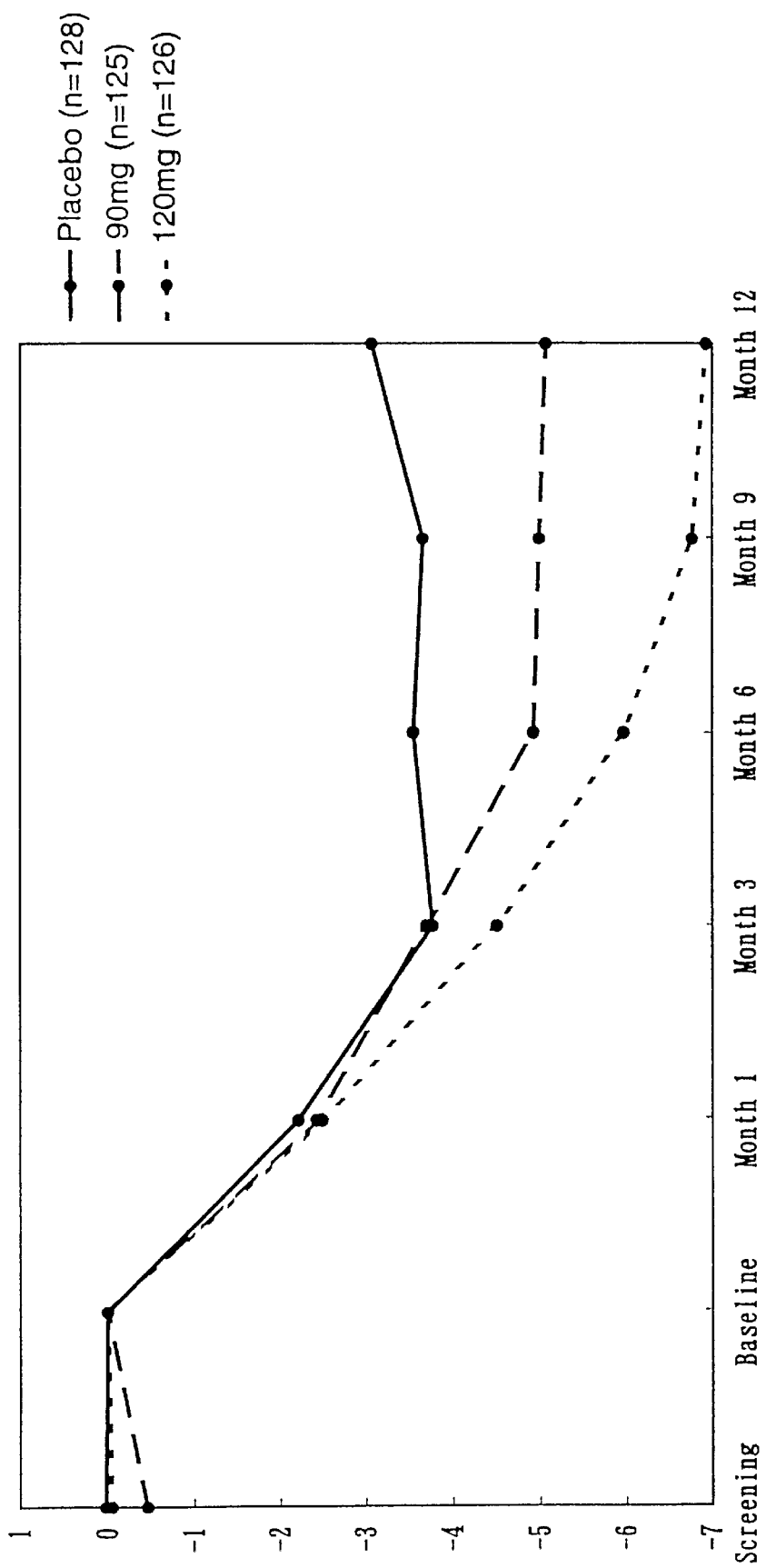
FIG. 2 shows the results of analysis of the clinical data obtained in Clinical Study Example 1, in terms of an efficacy parameter (ADAS Cognitive Score) shown in Clinical Study Example 1.
Figure 3:
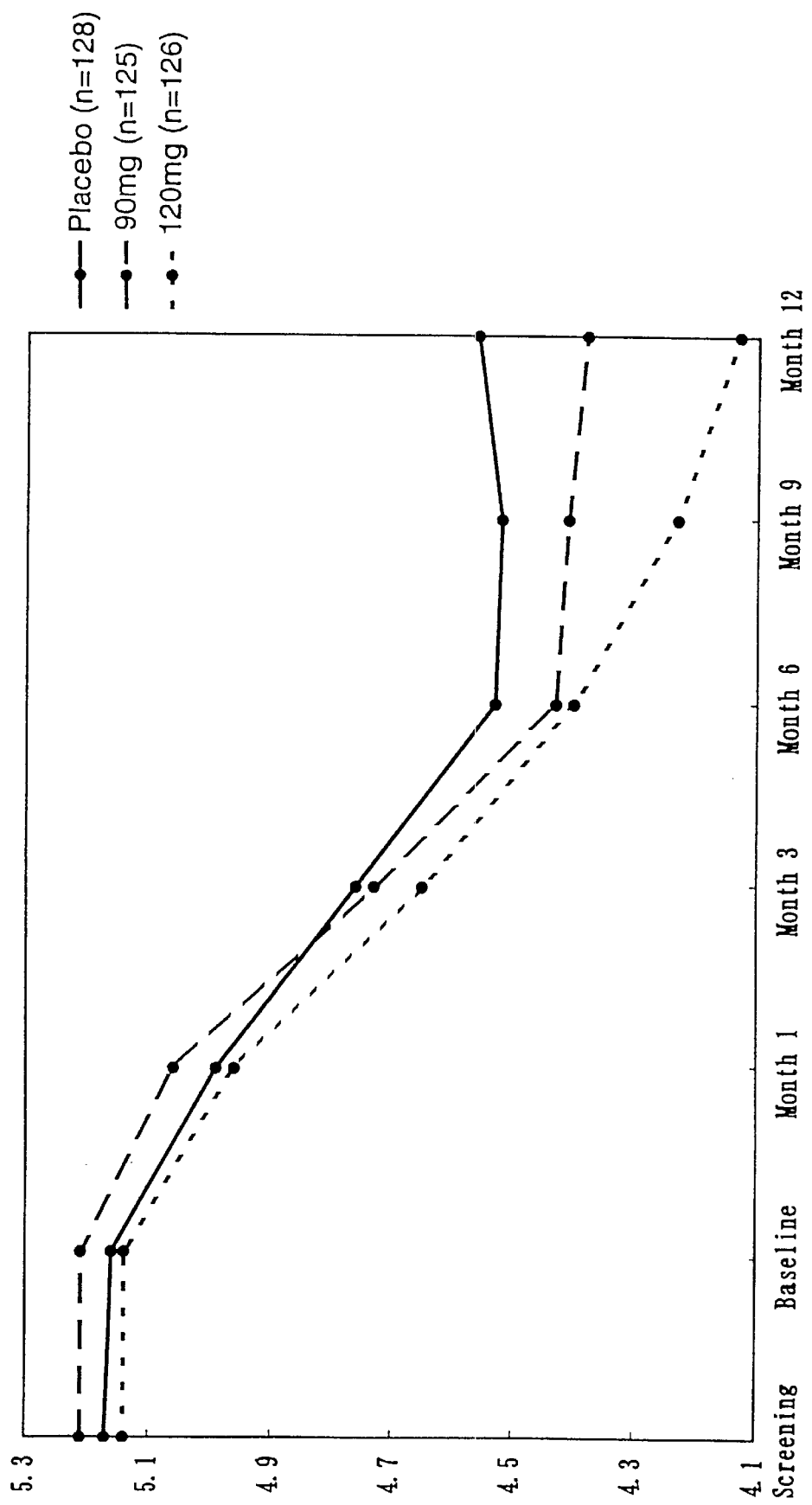
FIG. 3 shows the results of analysis of the clinical data obtained in Clinical Study Example 1, in terms of an efficacy parameter (CGI Severity of Disease) shown in Clinical Study Example 1.
Figure 4:
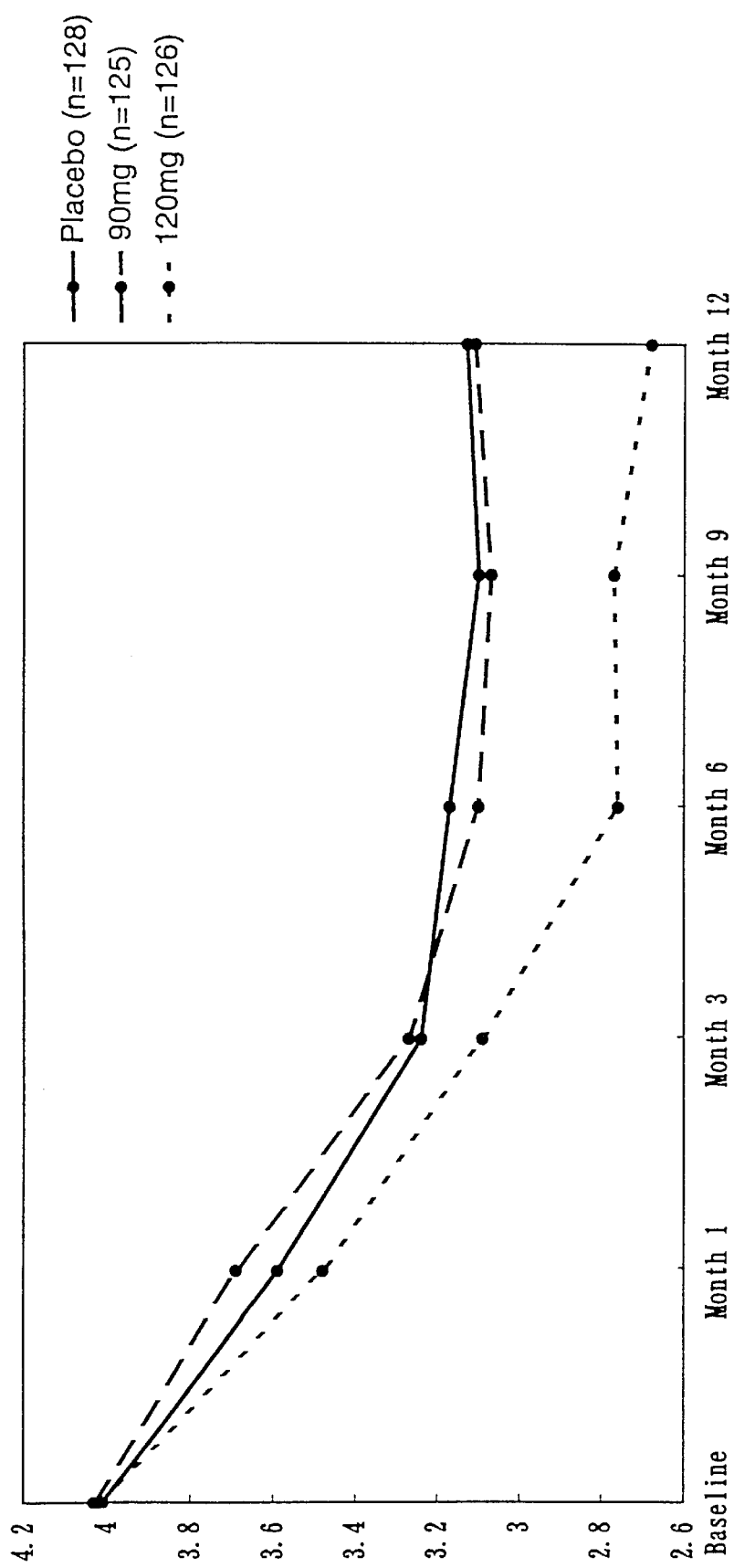
FIG. 4 shows the results of analysis of the clinical data obtained in Clinical Study Example 1, in terms of an efficacy parameter (CGI Global Improvement) shown in Clinical Study Example 1.
Figure 5:
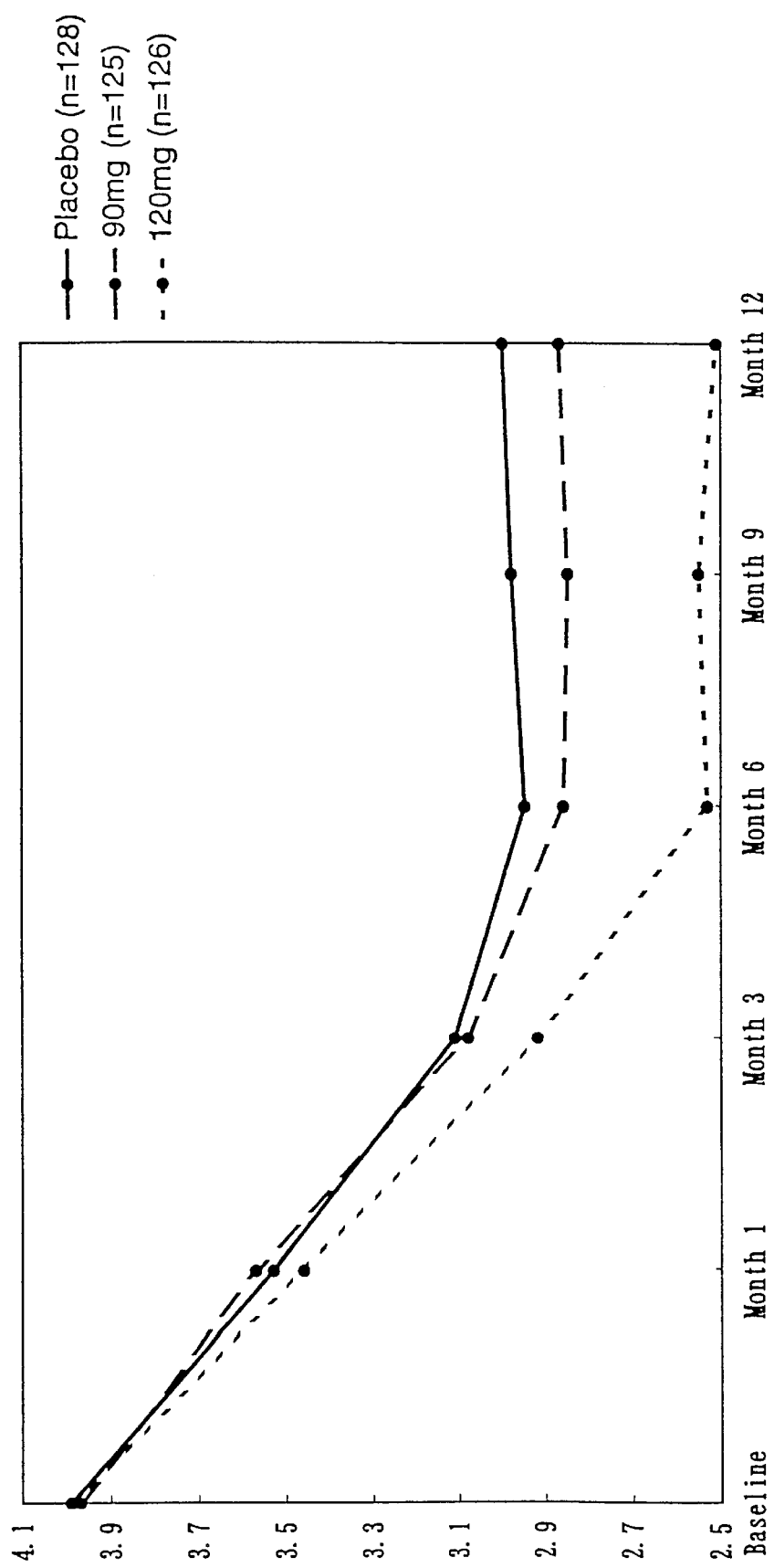
FIG. 5 shows the results of analysis of the clinical data obtained in Clinical Study Example 1, in terms of an efficacy parameter (CGI Therapeutic Effect) shown in Clinical Study Example 1.
Figure 6:
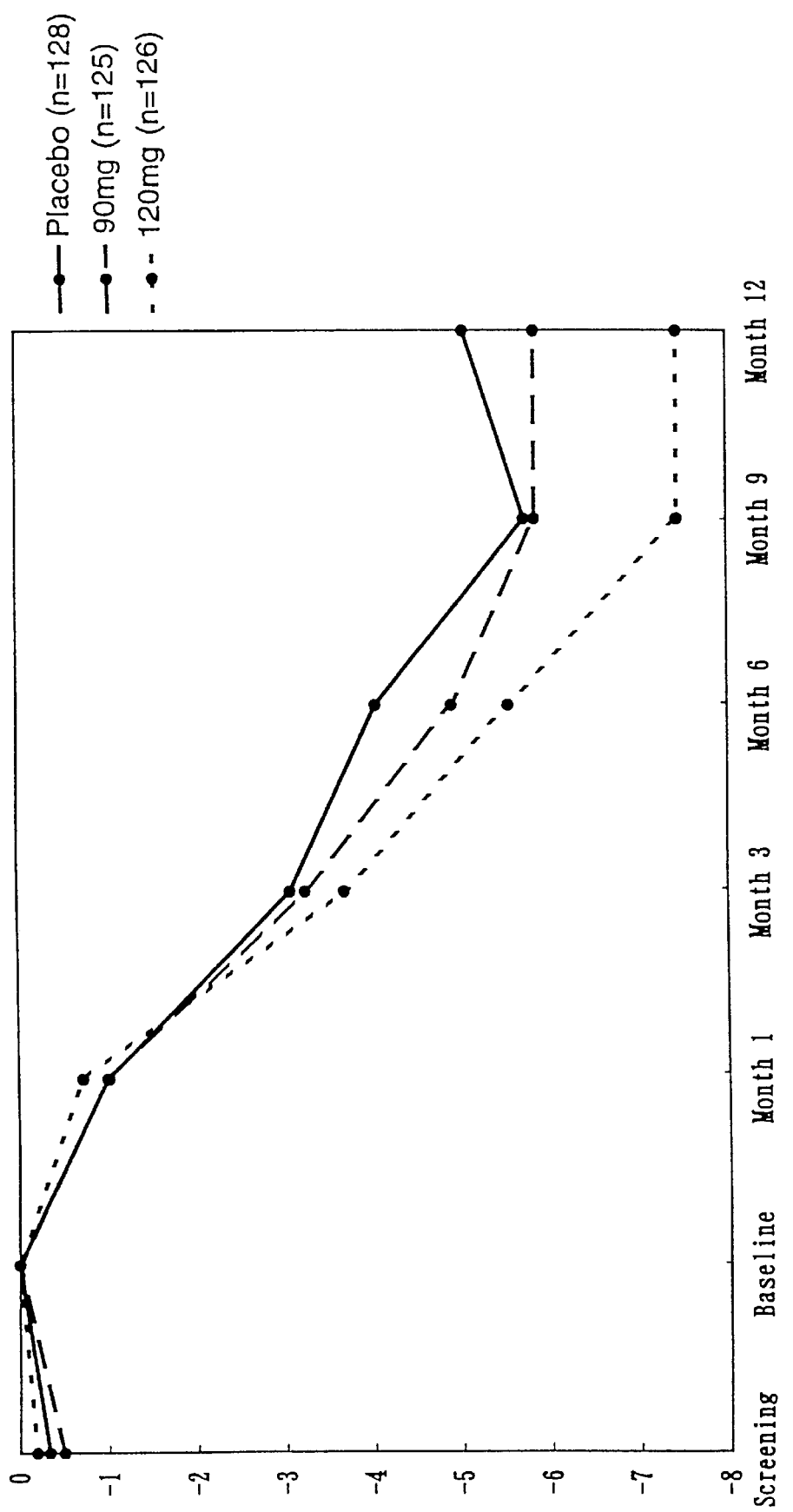
FIG. 6 shows the results of analysis of the clinical data obtained in Clinical Study Example 1, in terms of an efficacy parameter (NOSGER Sum Score) shown in Clinical Study Example 1.
Figure 7:
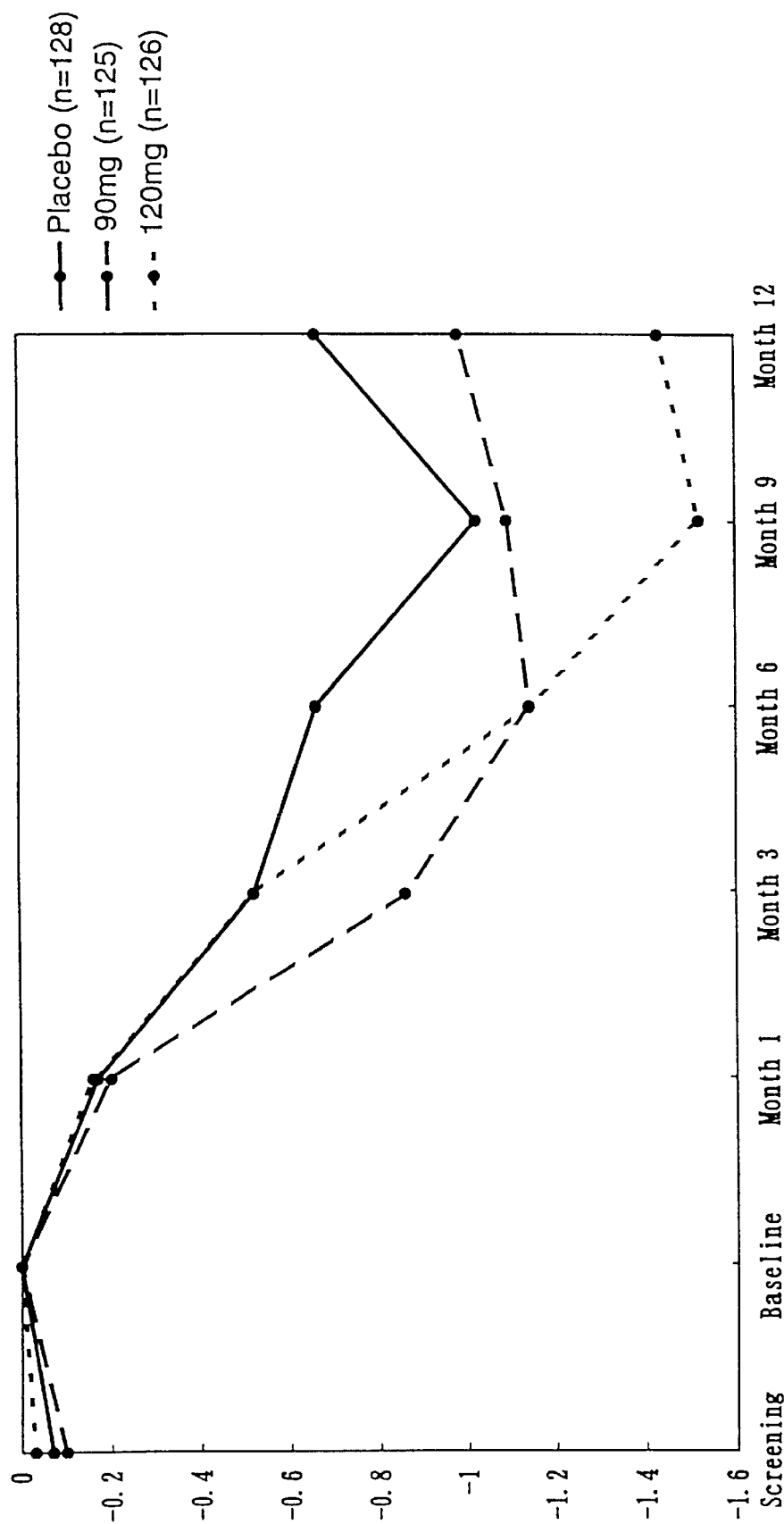
FIG. 7 shows the results of analysis of the clinical data obtained in Clinical Study Example 1, in terms of an efficacy parameter (NOSGER IADL) shown in Clinical Study Example 1.

The present invention relates to:

(1) a method for preventing or treating dementia, which comprises orally administering idebenone to a patient with dementia for more than 6 months, (2) the method of the above (1), wherein the dementia is of senile dementia Alzheimer's type, (3) the method of the above (1), wherein the dementia is Alzheimer's disease, (4) a method for preventing or treating dementia, which comprises orally administering idebenone to a patient with dementia at a daily dose of not less than about 270 mg and not more than about 360 mg for more than 6 months and not more than about 5 years, (5) a method for preventing or treating dementia, which comprises orally administering idebenone to a patient with dementia at a daily dose of not less than about 270 mg and not more than about 720 mg for more than 6 months and not more than about 5 years, (6) a method for prevention of the progression of dementia, which comprises orally administering of idebenone to a patient with dementia for more than 6 months, (7) a method for orally administering idebenone for more than 6 months for the treatment of dementia, (8) use of idebenone for the treatment of dementia, which comprises orally administering idebenone for more than 6 months, (9) a pharmaceutical composition for prevention of the progression of dementia, which comprises idebenone,

(10) the composition of the above (9), which effectively prevents the progression of dementia for more than 6 months,

(11) the composition of the above (9), which is orally administered for not less than about 1 year and not more than about 5 years,

(12) the composition of the above (9), which is orally administered for not less than about 2 years and not more than about 4 years,

(13) the composition of the above (9), which is orally administered at a daily dose of not less than about 270 mg of idebenone,

(14) the composition of the above (9), which is orally administered at a daily dose of not less than about 270 mg and not more than about 1,440 mg of idebenone,

(15) the composition of the above (9), which is orally administered at a daily dose of about 270 mg of idebenone,

(16) the composition of the above (9), which is orally administered at a daily dose of about 360 mg of idebenone,

(17) the composition of the above (9), which is orally administered at a daily dose of about 720 mg of idebenone,

(18) the composition of the above (9), which is administered 2 to 6 times a day at intervals of at least 4 hours,

(19) the composition of the above (9), which is orally administered 3 times a day,

(20) the composition of the above (9), which is administered after meals,

(21) the composition of the above (9), which is administered every day,

(22) the composition of the above (9), wherein the dementia is senile dementia of Alzheimer's type,

(23) the composition of the above (9), wherein the dementia is Alzheimer's disease,

(24) use of idebenone for manufacturing a pharmaceutical composition for prevention of the progression of dementia,

(25) a medicine comprising idebenone for preventing or treating dementia and orally administering idebenone for more than 6 months,

(26) the medicine of the above (25), which effectively prevents the progression of dementia,

(27) use of idebenone for the manufacture of a medicament for oral administration for preventing or treating dementia wherein said medicament is administered to a patient with dementia for more than 6 months,

(28) use of the above (27) in which the dementia is senile dementia of Alzheimer's type,

(29) use of the above (27) in which the dementia is Alzheimer's disease,

(30) use of any of the above (27) to (29) in which a daily dose of idebenone of not less than about 270 mg and not more than about 720 mg is administered for more than 6 months and not more than about 5 years,

(31) use of any of the above (27) to (29) in which a daily dose of idebenone of not less than about 270 mg and not more than about 360 mg is administered for more than 6 months and not more than about 5 years,

(32) use of idebenone for the manufacture of a medicament for prevention of the progression of dementia,

(33) use of idebenone for the manufacture of a medicament for oral administration for prevention of the progression of dementia wherein idebenone is administered to a patient with dementia for more than 6 months,

(34) use of idebenone for manufacturing a pharmaceutical composition for preventing or treating dementia which is administered to a patient for more than 6 months,

(35) use of any of the above (27), (32), (33) or (34) in which idebenone is administered for not less than about 1 year and not more than about 5 years,

(36) use of any of the above (27), (32), (33) or (34) in which idebenone is administered for not less than about 2 years and not more than about 4 years,

(37) use of any of the above (27), (32), (33) or (34) in which idebenone is administered at a daily dose of not less than about 270 mg,

(38) use of any of the above (27), (32), (33) or (34) in which idebenone is administered at a daily dose of not less than about 270 mg and not more than about 1,440 mg of idebenone,

(39) use of any of the above (27), (32), (33) or (34) in which idebenone is administered at a daily dose of about 270 mg of idebenone,

(40) use of any of the above (27), (32), (33) or (34) in which idebenone is administered at a daily dose of about 360 mg of idebenone,

(41) use of any of the above (27), (32), (33) or (34) in which idebenone is administered at a daily dose of about 720 mg of idebenone,

(42) use of any of the above (27), (32), (33) or (34) in which idebenone is administered 2 to 6 times a day at intervals of at least 4 hours,

(43) use of any of the above (27), (32), (33) or (34) in which idebenone is administered 3 times a day,

(44) use of any of the above (27) to (43) in which idebenone is administered after meals, and

(45) use of any of the above (27), (32) or (33) in which the medicament is administered every day.

The pharmaceutical for the present invention, idebenone, is described in, for example, JP-B-62 3134 (1987) and U.S. Pat. No. 4,139,545. Its chemical name is 6-(10-hydroxydecyl)-2,3-dimethoxy-5-methyl-1,4-benzoquinone.

Idebenone can be used in various dosage forms, including tablets, capsules, fine granules, granules and powders, as a pharmaceutical composition, in accordance with commonly known methods, such as those described in JP-B-1 12727 (1989) (U.S. Pat. No. 4,436,753), JP-B-63 51123 (1988) (U.S. Pat. No. 4,358,461), JP-B-1 39405 (1989) (U.S. Pat. No. 4,514,420), JP-A-3 81218 (EP-A-629400), and elsewhere. Although it may be used in any dosage form, as long as it permits long-term oral administration to patients with dementia, especially Alzheimer's disease or senile dementia of Alzheimer's type, tablets, fine granules and capsules are preferred. In the above forms, tablets containing not less than 30 mg of idebenone per tablet or capsules containing not less than 30 mg of idebenone per capsule are preferred.

Granules or fine granules respectively containing not less than 30 mg of idebenone per ingestion are preferred.

The pharmaceutical composition may incorporate commonly used excipients, binders, disintegrants, lubricants and other additives chosen as appropriate. The excipients include, for example, sucrose, lactose, glucose, starch, mannitol, sorbitol, cellulose, talc and cyclodextrin. The binders include, for example, cellulose, methyl cellulose, polyvinylpyrrolidone, gelatin, gum arabic, polyethylene glycol, sucrose and starch. The disintegrants include, for example, starch, carboxymethyl cellulose and calcium salt of carboxymethyl cellulose. The lubricants include, for example, talc. Also, idebenone may be used as a sustained-release preparation. The sustained-release preparation can be produced by per se known methods, for example, by coating tablets, granules, fine granules or capsules using oils and fats (e.g., triglyceride), polyglycerol fatty acid esters, hydroxypropyl cellulose and so on.

In the method for preventing or treating dementia and the method for prevention of the progression of dementia of the present invention, the dementia can be roughly divided into cerebral vascular dementia, senile dementia of Alzheimer's type and Alzheimer's disease. Mixed forms of dementia are included in the scope of the present invention. It is preferable that the method of the present invention be applied to senile dementia of Alzheimer's type and Alzheimer's disease.

When the above-described pharmaceutical composition containing idebenone is used to treat a patient with dementia or prevent (slow down) the progression of dementia, especially a patient with senile dementia of Alzheimer's type or Alzheimer's disease, the long-term administration period may have no limitation for the completion of the treatment or to substantially prevent the progression of dementia, as long as it is more than 6 months. According to an embodiment of the invention, the administration period is preferably not less than about 1 year and not more than about 5 years, more preferably not less than about 2 years and not less than about 4 years. Any of the long-term administration periods may be used with any dosage regime suitable according to the invention and described herein, or with any suitably adopted dosage regime.

The pharmaceutical composition of the present invention can be a medicine which describes "for preventing or treating dementia and orally administering idebenone for more than 6 months" in the package insert (explanation lieflet for use).

Any method of administration is acceptable, as long as it permits long-term administration. Oral administration is preferred. In such methods of administration, there is no limitation in the method adopted, and examples of the methods include consective administration every day and intermittent administration with medication-free intervals. In the intermittent administration, the medication-free interval is preferably 1 day to about 30 days. Specifically, the methods of intermittent administration include intermittent administration every two days, intermittent administration comprising cycles of 2 days of administration and a 1 day interval of non-administration, intermittent administration comprising cycles of 5 consecutive days of administration and a 2 day interval of non-administration (administration on Monday through Friday, interval on Saturday and Sunday), and the dosage form as calender tablets. The method is chosen as appropriate according to individual patients with senile dementia of Alzheimer's type or Alzheimer's disease.

During the above-described medication period, the dose may be varied as appropriate according to pathologic state and symptom change in the patient with dementia.

In the long-term administration of idebenone according to the invention, the dose of idebenone is about 90 mg to about 3,000 mg per day, preferably about 180 mg to about 1,500 mg per day, and more preferably about 270 mg to 1,440 mg per day, especially preferably about 270 mg to 720 mg per day.

Preferred dosages according to embodiments of the present invention include 3-times-a-day administration of 90 mg idebenone, 3-times-a-day administration of 120 mg idebenone, 3-times-a-day administration of 150 mg idebenone, 3-times-a-day administration of 180 mg idebenone, 3-times-a-day administration of 210 mg idebenone, 3-times-a-day administration of 240 mg idebenone, 3-times-a-day administration of 270 mg idebenone, 3-times-a-day administration of 300 mg idebenone, 3-times-a-day administration of 330 mg idebenone, 3-times-a-day administration of 360 mg idebenone, 3-times-a-day administration of 390 mg idebenone, 3-times-a-day administration of 420 mg idebenone, 3-times-a-day administration of 450 mg idebenone, and 3-times-a-day administration of 480 mg idebenone. The daily dose of idebenone may be varied as appropriate within the range of combinations of the above modes, for example, not less than about 270 mg and not more than about 360 mg, not less than about 270 mg and not more than about 630 mg, not less than about 360 mg and not more than about 450 mg, not less than about 540 mg and not more than about 630 mg, not less than about 270 mg and not more than about 720 mg and not less than about 720 mg and not more than about 1,440 mg, preferably not less than about 270 mg and not more than about 720 mg, more preferably not less than about 270 mg and not more than about 360 mg. For the purpose of prevention of the progression of dementia, the above doses may be lowered as appropriate whenever necessary.

The agent used in the therapeutic method of the present invention may be used in combination with idebenone and other agents exemplified by agents affecting the central nervous system such as acetylcholinesterase inhibitors (e.g. 8-[1-oxo-3-[1-(phenylmethyl)piperidin-4-yl]propyl]-2,3,4, 5-tetrahydro-1H-1-benzazepine fumarate described in U.S. Pat. No. 5,273,974, etc.), anxiolytics, hypnotics, antischizophrenia agents, antiparkinsonism agents and nootropic (cerebral circulation improvers and cerebral energy metabolism activators, etc.), antihypertensives, antidiabetic agents and agents for hyperlipidemia. It may also be used with nutrients such as vitamin preparations, digestion/absorption promoters, gastrointestinal agents, and so on.

Idebenone, used for the present invention, is very low in toxicity, having almost no adverse effects or toxicity even in long-term administration. For example, the acute toxicity $LD_{50}$ value of idebenone is not less than 10,000 mg/kg for both sexes in mice, and not less than 10,000 mg/kg in male rats and about 10,000 mg/kg in female rats.

Also, the hepatic clinical laboratory values (GPT and GOT values) obtained from patients with senile dementia of Alzheimer's type administered 90 mg of idebenone 3 times daily (270 mg per day) or 120 mg of idebenone 3 times daily (360 mg per day) for 6 months are shown in Table 1 below. As is evident from the table, idebenone caused unexpectedly little change in GPT level and GOT level when continuously administered at high doses for an extended period of time, with almost no difference from the control group (placebo group), demonstrating that its toxicity and adverse effects are very low.

In the prophylactic/therapeutic method or the method for prevention of the progression of dementia of the present invention, the dose of idebenone can be chosen as appropriate according to symptoms in the patient with dementia, especially with senile dementia of Alzheimer's type or Alzheimer's disease, and symptom progression rate, because of the safety of idebenone as mentioned above. The dose is normally not less than 90 mg per day, preferably not less than 270 mg per day. In the case of a sustained-release preparation of idebenone, it is administered so that the amount of idebenone released is not less than 90 mg per day, preferably not less than 150 mg per day. If the bioavailability of idebenone is improved, the above dose may be lowered as appropriate.

The daily dose of idebenone in the therapeutic method or the method for prevention of the progression of dementia according to the present invention may be administered in several portions daily as necessary. In such cases, the daily dose of idebenone is administered in 2 to 6 portions, preferably 3 portions, in one day. The dose per administration is obtained by dividing the daily dose by the number of administration in the day.

Although administration time is not subject to limitation, administration after every meal is preferred.

By administering idebenone by the long-term administration method of the present invention, various symptoms in patients with dementia, especially with senile dementia of Alzheimer's type or Alzheimer's disease, can be markedly mitigated. In addition to prevention of the progression of senile dementia of Alzheimer's type and Alzheimer's disease by long-term administration, the symptom-relieving effect is markedly higher than that obtained by the short-term treatment for less than 6 months.

The long-term administration according to the present invention is preferably by oral administration of idebenone to a patient with dementia, especially a patient with senile dementia of Alzheimer's type or Alzheimer's disease at a daily dose of not less than about 270 mg and not more than about 360 mg or not less than about 270 mg and not more than about 720 mg for more than 6 months and not more than about 5 years to prevent or treat dementia or to prevent the progression of dementia symptoms.

The pharmaceutical composition for prevention of the progression of dementia of the present invention can be advantageously used as a medicine because it can be administered safely and continuously for an extended period of time and because it markedly relieves various symptoms in dementia, surely prevents or suppresses the progression of dementia symptoms for an extended period of time, and exhibits an excellent prophylactic/therapeutic effect against dementia.

EXAMPLES

The present invention is hereinafter described in more detail by means of the following preparation examples, a clinical study example regarding the clinical effects (symptom-relieving and symptom progression-suppressing effects) of long-term administration of idebenone according to the present invention in patients with senile dementia of Alzheimer's type, and reference example, but is not limited by these examples, and may be modified, as long as the scope of the present invention is not deviated from.

Clinical Study Example 1

In patients with senile dementia of Alzheimer's type, a double-blind placebo controlled multicenter comparative study was conducted under the conditions shown below.

Subjects
  451 patients with senile dementia of Alzheimer's type (154 males, 297 females)
Doses and administration
  (1) Placebo administration
  (2) 3-times-a-day administration of 90 mg idebenone
  (3) 3-times-a-day administration of 120 mg idebenone
Administration periods
  1, 3, 6, 9, 12, 18 and 24 consecutive months
Case grouping
  Group 1 (3-times-a-day administration of 90 mg idebenone), 149 patients (42 males, 107 females; average age 70 years)
  Group 2 (3-times-a-day administration of 120 mg idebenone), 149 patients (58 males, 91 females; average age 70 years)
  Group 3 (placebo administration), 153 patients (54 males, 99 females; average age 70 years)
Number of participating institutions: 14
Administration method
  Oral administration just after every meal
Dosage form
  Tablets which cannot be discriminated between actual and placebo preparations obtained by the Preparation Examples 1 to 3 mentioned later (tablet dimensions: 11 mm diameter, 4.3 mm thickness, 415 mg weight)
Group-to-group bias
  There was no bias among the three groups in terms of background factors or pre-administration efficacy assessment scale values.
Efficacy parameters
  Primary efficacy parameter
    ADAS Sum Score
  Secondary efficacy parameters
    ADAS Cognitive Score
    CGI Severity of Disease
    CGI Global Improvement
    CGI Therapeutic Effect
    NOSGER Sum Score
    NOSGER IADL
    SKT
Safety assessment items
  Accompanying symptoms
  Clinical laboratory values
Abbreviations
  ADAS: Alzheimer's Disease Assessment Scale
  CGI: Clinical Global Impression Scale
  NOSGER: Nurse's Observation Scale for Geriatric Patients
  NOSGER IADL: Nurse's Observation Scale for Geriatric Patients in Instrumental Activities of Daily Living
  SKT: Syndrom-Kurz-Test
Reference
  Akira Honma and Masaomi Miyamoto Shinkei Seishin Yakuri, Vol. 16, No. 12, pp. 729–738 (1994)

In terms of the above-described primary efficacy parameter and secondary efficacy parameters, the therapeutic and preventing of the symptom progression effects of long-term administration of idebenone were assessed.
Analysis
  The analytical results obtained by the above-described assessment methods are shown in FIGS. 1 to 7.
Results
  1. ADAS Sum Score
  At both 6 and 12 months treatment, significant relief occurred in the 3-times-a-day administration of 90 mg idebenone group and the 3-times-a-day administration of 120 mg idebenone group compared with the placebo group, the effect being dose dependent.

In addition, the therapeutic effect obtained for a period exceeding 6 months was excellent.

2. ADAS Cognitive Score, CGI (above 3 items), NOSGER (above 2 items) and SKT

For all items, significant differences among the three groups were noted, with dose dependency. In addition, the therapeutic effect obtained for a period exceeding 6 months was excellent for all items.

3. Safety assessment results

No differences were noted among the three groups in terms of incidence and severity. The major objective and subjective symptoms were vertigo, anorexia, sleep disturbance and arthralgia. As shown in Table 1, the elevation of clinical laboratory values (GOT and GPT) in the idebenone administration groups was very low.

Table 1 List of Abnormal Clinical Laboratory Values (GPT and GOT)

These results demonstrate that long-term administration of idebenone, especially long-term administration at high doses, serves well as a therapeutic method for symptom relief or prevention (suppression) of symptom progression in patients with senile dementia of Alzheimer's type. When idebenone was administered for a period exceeding 6 months, in particular, as in the present clinical study, greater symptom-relieving and symptom progression-suppressing effects are noted at 12 months than at 6 months. In addition, in comparison with the published clinical data on tacrine, better effects were obtained in the 270 mg (90 mg, 3-times-a-day) and 360 mg (120 mg, 3-times-a-day) idebenone administration groups, irrespective of assessment method, with a marked effect in the 360 mg idebenone administration group. Furthermore, regarding safety of tacrine, a large number of dropouts or discontinuations occurred due to adverse reactions such as liver dysfunction during the study period, as stated above. For example, until final administration by 30 weeks, 59% of the subjects in the low-dose tacrine group, 71% in the moderate-dose group and 74% in the high-dose group had dropped out. By contrast, 9% of the subjects had dropped out by 6 months, and about 15% of the subjects had dropped out by 12 months in this study and the therapeutic method of the present invention using idebenone by far surpasses the conventional method in terms of safety.

Also, as shown in FIGS. 1 to 7, it is evident that symptom progression was surely suppressed, since a good relieving effect was obtained with a descending curve even after the placebo effect disappeared.

It is generally expected that as the pharmaceutical administration period increases, the therapeutic effect is diminished, while the incidence of adverse reactions increases. However, the long-term idebenone administration method of the present invention serves as a therapeutic method or prevention of the symptom progression method for senile dementia of Alzheimer's type excellent in both efficacy and safety. The therapeutic method of the present invention is therefore generally applicable to dementia.

Preparation Example 1

Production of tablets containing 90 mg of idebenone for clinical study

| | |
|---|---:|
| Idebenone | 90,000 g |
| Lactose (EP) | 233,186 g |
| Gelatinized starch | 11,210 g |
| Calcium salt of carboxymethyl cellulose (ECG 505) | 67,270 g |
| Magnesium stearate (EP) | 1,120 g |
| Hydroxypropylmethyl cellulose USP (Pharmacoat 606) | 5,573 g |
| Polyethylene glycol (NF 6000) | 1,393 g |
| Propylene glycol (EP) | 465 g |
| Talc (EP) | 1,858 g |
| Titanium oxide (EP E171) | 2,786 g |
| Red Color 30 (E172) | 139 g |
| Total | 415,000 g |

After idebenone and water were added to, and kneaded with, the above excipients for pharmaceutical preparations, the mixture was dried. To this dry kneaded product, the above disintegrants and lubricant were added, followed by uniform mixing, after which the whole mixture was compressed using a compressive tableting machine to yield 1,000,000 tablets 11 mm in diameter, 4.3 mm in thickness and 415 mg in weight which contained 90 mg of idebenone per tablet.

Preparation Example 2

Production of tablets containing 120 mg of idebenone for clinical study

| | |
|---|---:|
| Idebenone | 120,000 g |
| Lactose (EP) | 203,186 g |
| Gelatinized starch | 11,210 g |
| Calcium salt of carboxymethyl cellulose (ECG 505) | 67,270 g |
| Magnesium stearate (EP) | 1,120 g |
| Hydroxypropylmethyl cellulose USP (Pharmacoat 606) | 5,573 g |
| Polyethylene glycol (NF 6000) | 1,393 g |
| Propylene glycol (EP) | 465 g |
| Talc (EP) | 1,858 g |
| Titanium oxide (EP E171) | 2,786 g |
| Red Color 30 (E172) | 139 g |
| Total | 415,000 g |

| | | GPT Level (U/L) | | GOT Level (U/L) | |
|---|---|---|---|---|---|
| Patient Number | Drug Administered | Pre-administration | 6 Months of Administration | Pre-administration | 6 Months of Administration |
| 10 | placebo | 30 | 41 | 23 | 29 |
| 16 | placebo | 33 | 38 | 24 | 38 |
| 84 | placebo | 23 | 48 | 21 | 28 |
| 129 | placebo | 18 | 55 | 17 | 21 |
| 152 | placebo | 26 | 43 | 17 | 30 |
| 155 | placebo | 16 | 74 | 13 | 65 |
| 168 | placebo | 25 | 15 | 31 | 37 |
| 327 | placebo | 11 | 36 | 15 | 26 |
| 413 | placebo | 31 | 44 | 19 | 25 |
| 414 | placebo | 32 | 37 | 21 | 18 |
| 517 | placebo | 24 | 33 | 22 | 29 |
| 541 | placebo | 20 | 53 | 16 | 41 |
| 28 | 90 mg | 25 | 61 | 19 | 45 |
| 87 | 90 mg | 34 | 54 | 27 | 38 |
| 136 | 90 mg | 36 | 34 | 33 | 60 |
| 153 | 90 mg | 63 | 43 | 32 | 86 |
| 167 | 90 mg | 9 | 26 | 15 | 49 |
| 179 | 90 mg | 25 | 37 | 29 | 32 |
| 287 | 90 mg | 14 | 35 | 13 | 47 |
| 322 | 90 mg | 29 | 37 | 22 | 26 |
| 550 | 90 mg | 33 | 50 | 27 | 29 |
| 1 | 120 mg | 22 | 26 | 23 | 41 |
| 160 | 120 mg | 14 | 39 | 24 | 27 |
| 180 | 120 mg | 28 | 43 | 24 | 28 |
| 276 | 120 mg | 29 | 55 | 29 | 34 |
| 285 | 120 mg | 37 | 25 | 24 | 37 |
| 403 | 120 mg | 28 | 38 | 21 | 23 |
| 407 | 120 mg | 31 | 60 | 25 | 131 |

After idebenone and water were added to, and kneaded with, the above excipients for pharmaceutical preparations, the mixture was dried. To this dry kneaded product, the above disintegrants and lubricant were added, followed by uniform mixing, after which the whole mixture was compressed using a compressive tableting machine to yield 1,000,000 tablets 11 mm in diameter, 4.3 mm in thickness and 415 mg in weight which contained 120 mg of idebenone per tablet.

Preparation Example 3

Production of placebo tablets for clinical study

| | |
|---|---:|
| Yellow quinoline 70 (E194) | 2,340 g |
| L-orange 2 (E110) | 360 g |
| Lactose (EP) | 274,116 g |
| Corn starch | 112,630 g |
| Hydroxypropyl cellulose | 12,230 g |
| Magnesium stearate (EP) | 1,110 g |
| Hydroxypropylmethyl cellulose USP (Pharmacoat 606) | 5,573 g |
| Polyethylene glycol (NF 6000) | 1,393 g |
| Propylene glycol (EP) | 465 g |
| Talc (EP) | 1,858 g |
| Titanium oxide (EP E171) | 2,786 g |
| Red Color 30 (E172) | 139 g |
| Total | 415,000 g |

After yellow quinoline 70 and L-orange 2, instead of idebenone, and water were added to, and kneaded with, the above excipients for pharmaceutical preparations, the mixture was dried. To this dry kneaded product, disintegrants and lubricant were added, followed by uniform mixing, after which the whole mixture was compressed using a compressive tableting machine to yield 1,000,000 placebo tablets 11 mm in diameter, 4.3 mm in thickness and 415 mg in weight which contained no idebenone per tablet.

PREPARATION EXAMPLE 4

Production of fine granules of idebenone

| | |
|---|---:|
| Idebenone | 72 g |
| Lactose | 580 g |
| Corn starch | 240 g |
| Avicel PH-101 | 120 g |
| Avicel RC-591-NF | 120 g |
| Carboxymethyl cellulose calcium | 60 g |

Idebenone, lactose, corn starch, Avicel PH-101 (produced by Asahi Chemical Industry), Avicel RC-591-NF and carboxymethyl cellulose calcium ECG-505 (produced by Gotoku Yakuhin) were charged into a tumbling fluidized granulating machine (MP-01, produced by Powrex Corporation) and subjected to fluidized thermal mixing at a rotor rotation rate of 250 rpm, while 60° C. hot air was blown at about 0.7 m$^3$/min. During this operation, the apparently yellow-orange to red idebenone was found to be punctate in a mixture with other starting materials. The air supply temperature was 60° C., a level slightly higher than the melting point of idebenone, 54.2° C. As the starting material charge temperature rose gradually, the idebenone melted and became generally pale orange; the idebenone was found to become a nearly uniform mixture with the excipients. Granulation and drying were then conducted, while the binder solution was sprayed by an ordinary method. The granules were taken from the granulating machine and classified by size to yield granules which passed a 30 mesh sieve but which remained on a 150 mesh sieve.

PREPARATION EXAMPLE 5

Production of fine granules of idebenone Charge formulation:

| | |
|---|---:|
| Lactose | 580 g |
| Corn starch | 220 g |
| Avicel PH-101 | 120 g |
| Avicel RC-591-NF | 120 g |
| Carboxymethyl cellulose calcium | 60 g |
| Binder formulation: | |
| Idebenone | 72 g |
| Corn starch | 20 g |

Corn starch was dissolved in distilled water to yield a corn starch solution. While stirring, this solution was heated to the gelatinizing temperature to achieve appropriate gelatinization. The gelatinized product was then cooled near the melting (dissolving) temperature of idebenone, followed by idebenone charging and dissolution under stirring, to yield an idebenone-containing binder solution, which was then incubated so that the idebenone did not solidify.

Separately, lactose, corn starch, Avicel PH-101, Avicel RC-591-NF and carboxymethyl cellulose calcium ECG-505 were charged into a tumbling fluidized granulating machine (MP-01, produced by Powrex Corporation).

Granulation was then conducted, while the idebenone-containing binder solution was sprayed by an ordinary method so that the idebenone did not solidify. The granules were then dried and taken from the granulating machine and classified by size to yield granules which passed a 30 mesh sieve but which remained on a 150 mesh sieve.

Reference Example 1

The ameliorative effect of the combined use of idebenone and 8-[1-oxo-3-(phenylmetyl)piperidin-4-yl]propyl]-2,3,4, 5-tetrahydro-1H-1-benzazepine fumarate (Compound A) on learning deficits was investigated in old rats.

Methods

Male young (3 months old) rats of the Fischer 344 strain and male old (27 months old) rats of the Fischer 344 strain were used.

The old rats were divided into the following four groups.

1) Control group: Saline.
2) Idebenone group: Repeated oral administration of idebenone 3 mg/kg.
3) Compound A group: Repeated oral administration of Compound A 0.3 mg/kg.
4) Combination group: Repeated oral administration of idebenone 3 mg/kg and Compound A 0.3 mg/kg.

In the combination group, idebenone was administered 30 minutes after administration of Compound A.

Passive avoidance learning tests were started on day 14 of treatment, and Morris water maze learning tests on day 20 of treatment.

On each day of experiment, idebenone and Compound A were administered 1 hour and 30 minutes, respectively, before initiation of the trial.

1. Passive avoidance learning

The passive avoidance learning test was performed using a chamber consisting of light and dark compartments. Young rats (saline, 10 animals) and old rats (control group, 9 animals; idebenone group, 7; Compound A group, 8; combination group, 8) were individually placed in the light compartment and 10 seconds later, the sliding door was opened. After a rat moved to the dark compartment, the rat was kept there for about 10 seconds with the door closed. One to two hours after such habituation trials, acquisition trials were performed.

In acquisition trials, after a rat moved to the dark compartment, a foot shock (0.4 mA, 3 seconds) was given through the grid floor. Retention trials were performed 24 hours after acquisition trials.

In each trial, the latency from opening of the slide door till the animal moved to the dark compartment (step-through latency) was measured.

2. Morris water maze learning

The water maze learning test was performed on young rats (saline, 10 animals) and old rats (control group, 7 animals; idebenone group, 6; Compound A group, 6; combination group, 6).

In pretraining which was performed for swimming training and motivation for escaping from water, four trials were performed using a water bath, 80 cm in diameter, in a condition that the platform was visible. From the following day, using a water bath, 120 cm in diameter, learning trials, one session (four trials) per day, were performed with the platform being placed below the water.

Results

1. Passive avoidance learning

There were no differences in latencies in habituation trials and acquisition trials between old and young rats. Drug treatment had no influence on the latencies.

Figure 8:
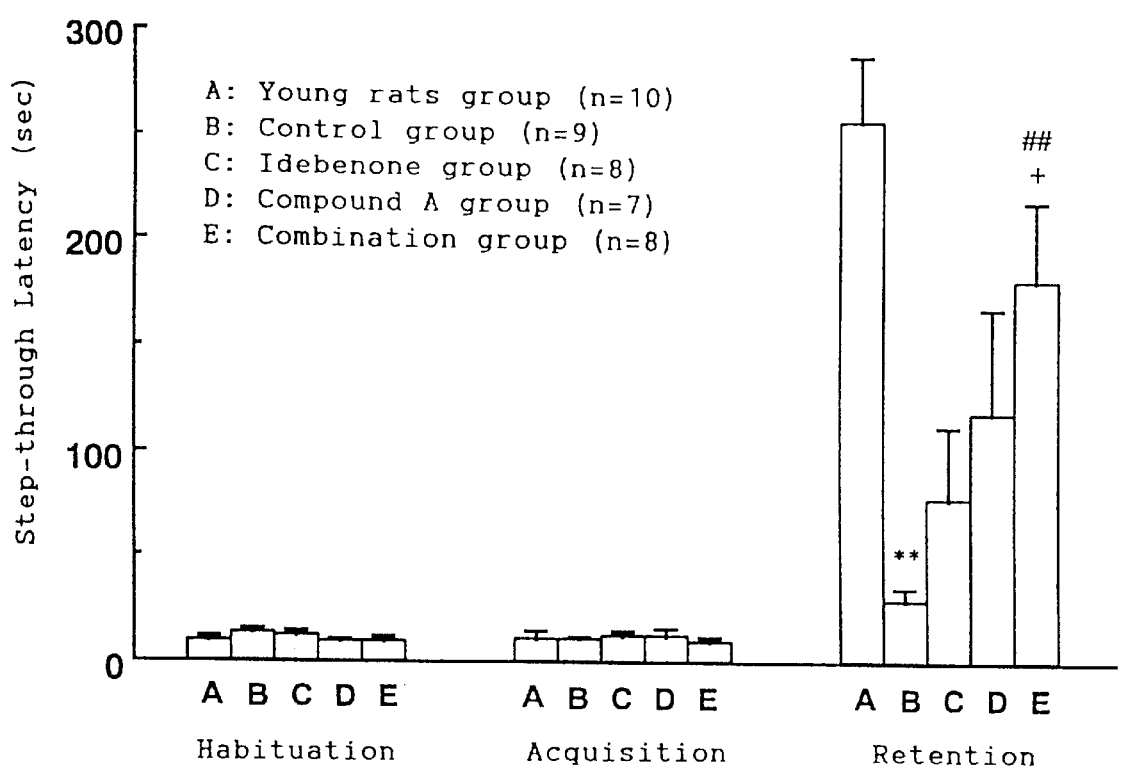
FIG. 8 shows the results of analysis of the data obtained in Reference Example 1, in terms of passive avoidance learning.

In the retention trials performed 24 hours after shock loading, the idebenone group and the Compound A group tended to show improvements in learning deficit in old rats but the effect was not significant. On the other hand, the combination group showed significant improvement compared with the control group (FIG. 8).

These results indicate that treatment with idebenone alone or Compound A alone did not improve passive avoidance learning deficit in old rats, whereas the combination of idebenone and Compound A improved the learning deficit in old rats.

2. Water maze learning

There was no difference between the groups in the latency to find the platform in the pretraining for the purposes of swimming training and motivation for escaping form the water.

Figure 9:
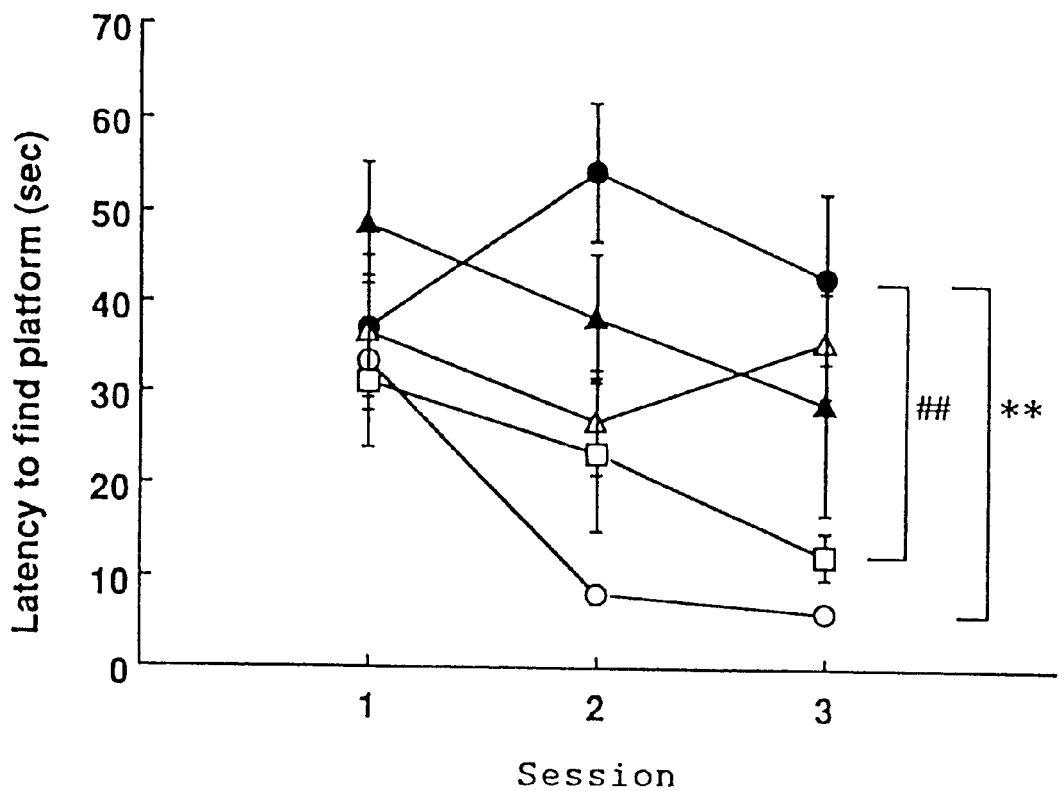
FIG. 9 shows the results of analysis of the data obtained in Reference Example 1, in terms of Morris water maze learning.

The average latencies to find the platform in the subsequent water maze learning tests are shown in FIG. 9, with four trials a day being taken as one session.

In the control group, the latency was little shortened by training. The idebenone group showed a slight tendency toward improvement in water maze learning deficit in the latter period of training. The Compound A group showed significant improvement on day 2 of experiment but did not differ from the control group on day 3. On the other hand, the combination group showed a marked improvement on days 2 and 3 of experiment.

The analysis of the results in FIG. 9 by two-way analysis of variance showed significant differences (F(4,30)=9.49, P<0.01) between the groups and an effect of training (F(2, 60)=7.06, P<0.01).

Group comparison of average latencies to find the platform for all trials revealed that the control group showed significant prolongation as compared with young rats (P<0.01), indicating an overt learning deficit. The idebenone group and the Compound A group did not show significant shortening of average latency compared with the control group, while the combination group showed significant shortening of latency compared with the control group (P<0.01).

These results indicate that treatment with idebenone alone or Compound A alone did not improve water maze learning deficit in old rats, whereas combination of idebenone and Compound A improved water maze learning deficit in old rats.

We claim:

1. A method for prevention of the progression of dementia, which comprises orally administering an effective amount of idebenone to a patient with dementia for not less than about 1 year and not more than about 5 years.

2. A method as claimed in claim 1, wherein the dementia is senile dementia of Alzheimer's type.

3. A method as claimed in claim 1, wherein the dementia is Alzheimer's disease.

4. A method as claimed in claim 1, wherein a daily dose of idebenone of not less than about 270 mg and not more than about 360 mg is administered.

5. A method as claimed in claim 1, wherein a daily dose of idebenone of not less than about 270 mg and not more than about 720 mg is administered.

6. A method as claimed in claim 1, wherein a daily dose of idebenone of not less than about 270 mg and not more than about 1,440 mg is administered.

7. A method as claimed in claim 1, wherein a daily dose of idebenone of about 270 mg is administered.

8. A method as claimed in claim 1, wherein a daily dose of idebenone of about 360 mg is administered.

9. A method as claimed in claim 1, wherein a daily dose of idebenone of about 720 mg is administered.

10. A method as claimed in claim 1, wherein idebenone is administered for not less than about 2 years and not more than about 4 years.

11. A method as claimed in claim 1, wherein idebenone is administered 2 to 6 times a day at intervals of at least 4 hours.

12. A method as claimed in claim 1, wherein idebenone is administered 3 times a day.

13. A method as claimed in claim 1, wherein idebenone is administered after meals.

14. A method as claimed in claim 1, wherein idebenone is administered every day.

15. A method as claimed in claim 1, wherein idebenone is administered after meals 3 times every day and at a daily dose of idebenone not of less than about 270 mg and not more than about 1,440 mg.

16. A method according to claim 12, wherein each dosage amount is 360 mg.

* * * * *